(12) United States Patent
Bezvershenko et al.

(10) Patent No.: US 7,760,918 B2
(45) Date of Patent: Jul. 20, 2010

(54) IDENTIFICATION OF A PERSON BASED ON ULTRA-SOUND SCAN ANALYSES OF HAND BONE GEOMETRY

(76) Inventors: Zinayida Bezvershenko, 252 Alderbrae Ave., Toronto, Ontario (CA) M8W 4K7; Volodymyr Tchouikevitch, 412-2361 Lakeshore Blvd. West, Toronto, ON (CA) M8V 1B7; John Ghorayeb, 524 Village Pkwy., Markham, ON (CA) L3R 9N5

( * ) Notice: Subject to any disclaimer, the term of this patent is extended or adjusted under 35 U.S.C. 154(b) by 149 days.

(21) Appl. No.: 12/190,902

(22) Filed: Aug. 13, 2008

(65) Prior Publication Data

US 2009/0043202 A1 Feb. 12, 2009

Related U.S. Application Data

(63) Continuation-in-part of application No. 10/910,303, filed on Aug. 4, 2004, now Pat. No. 7,428,319.

(30) Foreign Application Priority Data

Aug. 6, 2003 (CA) .................................. 2438220

(51) Int. Cl.
 G06K 9/00 (2006.01)
 G06K 9/62 (2006.01)
 G06K 9/68 (2006.01)
(52) U.S. Cl. .................. 382/115; 382/209; 382/218
(58) Field of Classification Search ............. 382/115, 382/131, 209, 218, 224, 305
See application file for complete search history.

(56) References Cited

U.S. PATENT DOCUMENTS

| | | | |
|---|---|---|---|
| 3,576,537 A | 4/1971 | Ernst |
| 3,576,538 A | 4/1971 | Miller |
| 3,581,282 A | 5/1971 | Altman |
| 3,648,240 A | 3/1972 | Jacoby et al. |
| 3,882,462 A | 5/1975 | McMahon |
| 3,968,476 A | 7/1976 | McMahon |
| 3,975,711 A | 8/1976 | McMahon |
| 4,032,889 A | 6/1977 | Nassimbene |
| 4,206,441 A | 6/1980 | Kondo |

(Continued)

FOREIGN PATENT DOCUMENTS

CA 2308381 11/1998

OTHER PUBLICATIONS

S. Bianchi, C. Martinoli, D. Sureda and G. Rizzatto, "Ultrasound of the Hand," "European Journal of Ultrasound," 2001, vol. 14, No. 1, pp. 29-34.

(Continued)

*Primary Examiner*—Daniel G Mariam
(74) *Attorney, Agent, or Firm*—Ogilvy Renault LLP

(57) ABSTRACT

A method for producing a model of bone geometry of a volumetric region of a body is provided. The method comprises scanning the volumetric region using ultrasound and acquiring geometric data associated with bones; identifying points derived from a surface of the bones; organizing the points into separate bone entities and transforming the points so as to position the bone entities in accordance with a normalized template. The model may be used for identifying or verifying the identity of a person.

20 Claims, 11 Drawing Sheets

U.S. PATENT DOCUMENTS

| | | | |
|---|---|---|---|
| 4,394,773 | A | 7/1983 | Ruell |
| 4,537,484 | A | 8/1985 | Fowler et al. |
| 4,573,193 | A | 2/1986 | Shuto et al. |
| 4,720,869 | A | 1/1988 | Wadia |
| 4,736,203 | A | 4/1988 | Sidlauskas |
| 4,792,226 | A | 12/1988 | Fishbine et al. |
| 4,857,916 | A | 8/1989 | Bellin |
| 4,977,601 | A | 12/1990 | Bicz |
| 5,045,940 | A | 9/1991 | Peters et al. |
| 5,073,950 | A | 12/1991 | Colbert et al. |
| 5,131,038 | A | 7/1992 | Puhl et al. |
| 5,325,442 | A | 6/1994 | Knapp |
| 5,335,288 | A | 8/1994 | Faulkner |
| 5,483,601 | A | 1/1996 | Faulkner |
| 5,515,298 | A | 5/1996 | Bicz |
| 5,647,364 | A | 7/1997 | Schneider et al. |
| 5,719,950 | A | 2/1998 | Osten et al. |
| 5,737,439 | A | 4/1998 | Lapsley et al. |
| 5,787,187 | A | 8/1998 | Bouchard et al. |
| 5,793,881 | A | 8/1998 | Stiver et al. |
| 5,892,838 | A | 4/1999 | Brady |
| 5,935,071 | A | 8/1999 | Schneider et al. |
| 6,092,192 | A | 7/2000 | Kanevsky et al. |
| 6,219,439 | B1 | 4/2001 | Burger |
| 6,219,639 | B1 | 4/2001 | Bakis et al. |
| 6,296,610 | B1 | 10/2001 | Schneider et al. |
| 6,336,045 | B1 | 1/2002 | Brooks |
| 6,343,140 | B1 | 1/2002 | Brooks |
| 6,421,453 | B1 | 7/2002 | Kanevsky et al. |
| 6,483,929 | B1 | 11/2002 | Murakami et al. |
| 6,507,662 | B1 | 1/2003 | Brooks |
| 6,628,810 | B1 | 9/2003 | Harkin |
| 6,720,712 | B2 | 4/2004 | Scott et al. |
| 6,724,689 | B2 | 4/2004 | Koenig |
| 6,844,660 | B2 | 1/2005 | Scott |
| 6,862,253 | B2 | 3/2005 | Blosser et al. |
| 6,898,299 | B1 | 5/2005 | Brooks |
| 7,190,817 | B1 | 3/2007 | Schneider et al. |
| 7,236,616 | B1 | 6/2007 | Scott |
| 7,254,255 | B2 | 8/2007 | Dennis |
| 2002/0053857 | A1 | 5/2002 | Scott et al. |
| 2002/0162031 | A1 | 10/2002 | Levin et al. |
| 2003/0001459 | A1 | 1/2003 | Scott |
| 2003/0133596 | A1 | 7/2003 | Brooks |
| 2004/0088553 | A1 | 5/2004 | Levin et al. ............ 713/186 |

OTHER PUBLICATIONS

R. D. Danese, A.A. Licata, "Ultrasound of the Skeleton: Review of its Clinical Applications and Pitfalls," "Current Rheumatology Reports," 2001, vol. 3, pp. 245-248.

T. Kahana, J. Hiss, P. Smith, "Quantitative Assessment of Trabecular Bone Pattern Identification," "Journal of Forensic Sciences," 1998, vol. 39, No. 5, pp. 1144-1147.

T. Kahana, J. Hiss, "Positive Identification by Means of Trabecular Bone Pattern Identification," "Journal of Forensic Sciences," 1994, vol. 39, No. 5, pp. 1325-1330.

Department of Computer Science, Hong Kong University of Science and Technology, HongKong, 2003, 8 p.

S. A. Teefey, W.D. Middleton, M. I. Boyer, "Sonography of the Hand and Wrist," "Seminars Ultrasound, CT, and MRI," 2000, 21(3). pp. 192-204.

Skokowski Can Biometric Defeat Terror?, Stanford University, pp. 1-12, Feb. 2002.

Vitria "Sistemed Biometrics", pp. 1-23, 1999.

IDENTIFICATION OF A PERSON BASED ON ULTRA-SOUND SCAN ANALYSES OF HAND BONE GEOMETRY

CROSS REFERENCE TO RELATED APPLICATION

This application is a continuation-in-part of U.S. patent application Ser. No. 10/910,303 filed Aug. 4, 2004, entitled "Identification of a Person Based on Ultra-Sound Scan Analyses of Hand Bone Geometry", which is incorporated herein by reference in its entirety.

TECHNICAL FIELD

The application relates generally to biometric identification methods and, more particularly, to a method for producing a model of bone geometry using ultrasound.

BACKGROUND OF THE ART

Biometric identification methods are ubiquitous and have been employed in many areas as a means of ensuring security through personal verification. Established biometric identification methods include the use of fingerprints, hand geometry, iris, retina, voice recognition, handwriting, etc. The prior art identifies limitations to the reliable use of some of these methods due to difficulty acquiring the necessary details to make correct verifications, or due to logistical problems in employing the method of verification in the same manner each and every time.

Wadia (U.S. Pat. No 4,720,869) and Sidlauskas (U.S. Pat. No 4,736,203) have explored the use of hand surface geometry for the purpose of biometric identification. Wadia's use of a two-dimensional optical scanner to process the data to develop invariable hand measurements, and Sidlauskas' use of a digitizing camera and a pair of orthogonal reflecting surfaces to obtain a three-dimensional image of a hand have both been successful methods for identification. However, since the application of these methods rely on the soft-tissue dimensions of the hand, these methods are limited by the potential environmental and physiological factors that may alter the dimensions of the surface of the hand. Moreover, trials with this methodology have revealed that it is possible to falsify authentication.

Traditionally, plain radiographs, CT, and MRI have been used to evaluate the hand and wrist. However, recent advances in technology have allowed ultrasound to be considered one of the first line imaging techniques in the assessment of this entity. Ultrasound is an attractive option to analyze bone geometry because it is inexpensive, non-invasive, rapid and lacks the radiation exposure that often accompanies the traditionally preferred modalities.

Accordingly, there is a need for a method for biometric identification using ultrasound.

SUMMARY

In one aspect, there is provided a method for producing a model of bone geometry of a volumetric region of a body, the method comprising the steps of:
  a) scanning the volumetric region using ultrasound and acquiring geometric data associated with bones within the volumetric region;
  b) identifying points from the acquired data that are derived from a surface of the bones;
  c) organizing the points into separate bone entities representing the bones of the volumetric region; and
  d) transforming the points so as to position the bone entities in accordance with a normalized template.

In a second aspect, there is provided a method for verifying the identity of a person based on ultrasound scan analysis of bone geometry, the method comprising the steps of:
  a) scanning a volumetric region of the person using ultrasound and acquiring geometric data associated with bones within the volumetric region;
  b) identifying points from the acquired data that are derived from a surface of the bones;
  c) organizing the points into separate bone entities representing the bones of the volumetric region;
  d) transforming the points so as to position the bone entities in accordance with a normalized template; and
  e) comparing the points of the acquired data to previously stored geometric data to determine if a match exists.

In a third aspect, there is provided a method for identifying a person based on ultrasound scan analysis of bone geometry, the method comprising the steps of:
  a) scanning a volumetric region of the person using ultrasound and acquiring geometric data associated with bones within the volumetric region;
  b) identifying points from the acquired data that are derived from a surface of the bones;
  c) organizing the points into separate bone entities representing the bones of the volumetric region;
  d) transforming the points so as to position the bone entities in accordance with a normalized template; and
  e) searching through previously stored geometric data comprising a plurality of templates, and, determining if a match exists between the points of the acquired data and one of the templates.

The method of biometric identification of an individual based on ultra-sound scan analyses of bones, such as hand bones, is unique in its own characteristics, and attempts to overcome the limitations suggested by the prior art. This new method uses a very inexpensive and safe means to acquire the data via ultra-sound scanning of the hand bones. Research has established that trabecular bone architecture is unique to each individual and stable enough to be used as a means for positive identification. Therefore, in one exemplary embodiment, the method attempts to identify an individual based on his/her hand bone geometry, because hand bones are unique to each person, and because the method to acquire the data is inexpensive, safe, accurate, and a non-invasive tool.

Further details of these and other aspects of the present invention will be apparent from the detailed description and figures included below.

DESCRIPTION OF THE DRAWINGS

Reference is now made to the accompanying figures, in which.

DETAILED DESCRIPTION OF THE PREFERRED EMBODIMENTS

The following text provides a thorough description of the "Identification" and "Normalized Template Building" algorithms with reference to a number of figures for ease of explanation. For a brief overview of the aforementioned algorithms, please refer to FIG. 1 and FIG. 2 respectively.

Even though the exemplary embodiment described below refers to a person's hand, it is understood that other volumetric regions of a body comprising bones could also be used. It is understood that the method is not limited to humans but could also be used on animals.

Figure 1:
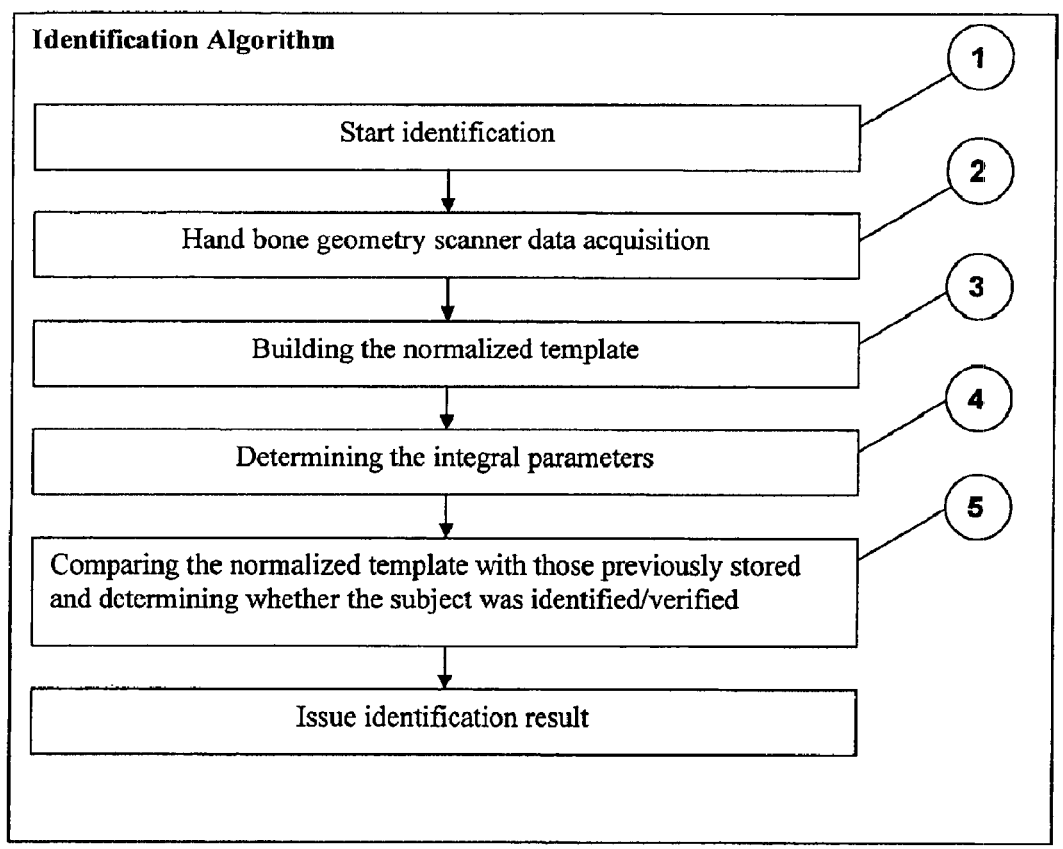
FIG. 1 is a schematic illustration of a method used for the identification or the verification of a person's identity based on bone geometry in accordance with one embodiment of the present invention.

Referring now to FIG. 1, the steps of a method for producing a model of bone geometry and for identifying or verifying the identity of a person are described below.

FIG. 1, Step 1: "Start Identification"

A volumetric region comprising bones is firstly scanned using ultrasound. For example, a person or subject may place the volumetric region such as a hand on a scanner platen for scanning. Once the subject chooses his/her left or right hand for scanning, at each subsequent identification attempt, the subject must use the same hand that was stored into the record carrier that can be placed on the host or a remote computer. In the case of a remote computer, the data may be transmitted and/or searched through an existing network via suitable communication means such as wireless communication for example. The hand can be placed in any direction or location within the parameters of the scanner platen because the inventor-created normalization technique transforms scan data to the normalized template, which is then used in the process of comparing and judging whether the scan matches previously stored data in the record carrier. As mentioned above, the method is user-friendly and flexible in the sense that the person's hand does not need to be positioned in a fixed place and in a specific alignment to be scanned and processed for comparison. However, this method may optionally make use of fixed positioning by means such as an indicator, an indentation or any other suitable means.

FIG. 1, Step 2: "Hand Bone Geometry Scanner Data Acquisition"

Figure 3:
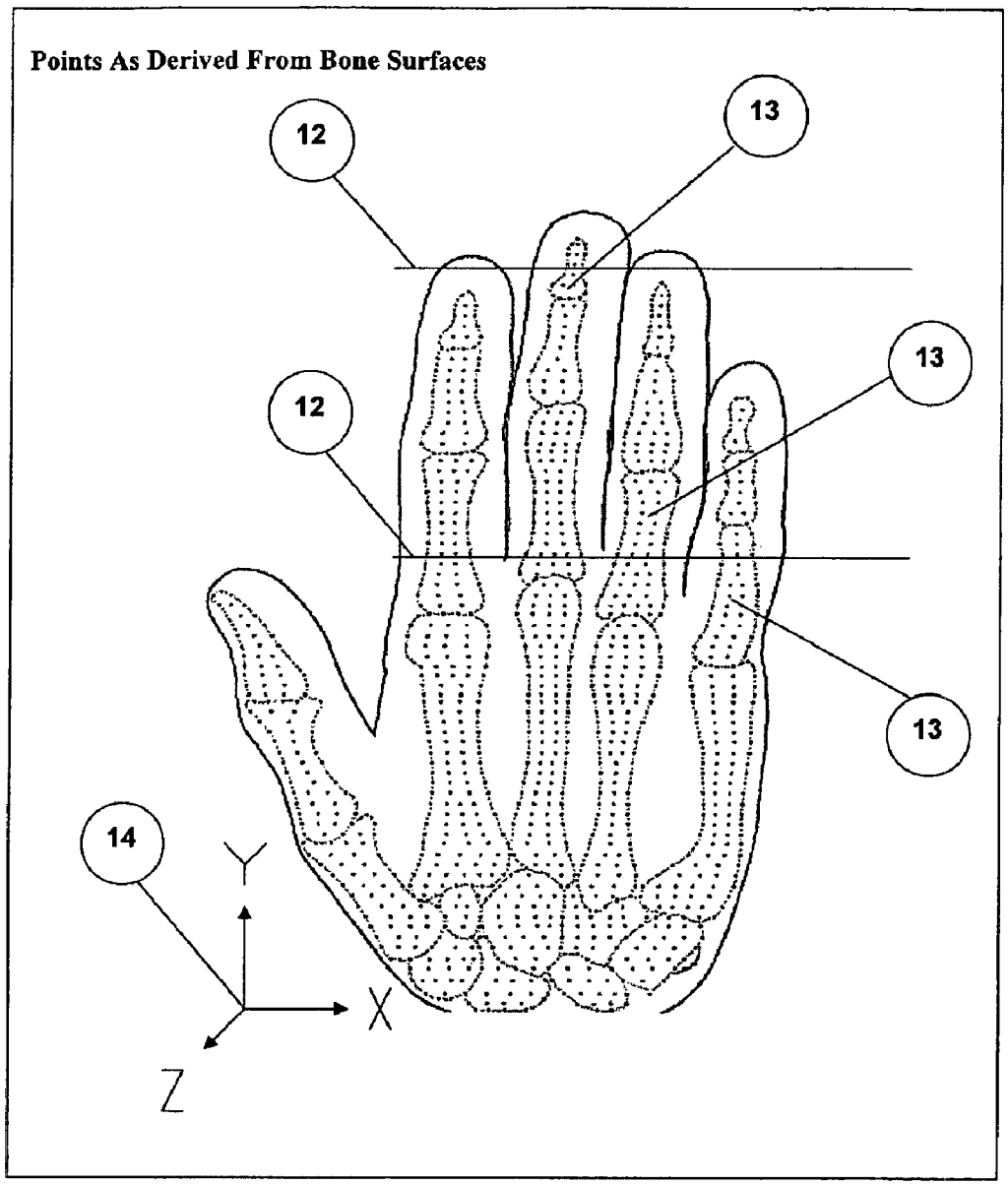
FIG. 3 is a top plan view of a hand of a person showing bones of the hand and acquired points derived from surfaces of the bones in relation to an absolute coordinate system of the hand.

The hand bone geometry data may be acquired using a freehand high-resolution ultrasound scanner (not shown). The data acquisition is not limited to any particular method or apparatus for transmitting ultrasonic energy. The process involves the acquisition of a set of 2D data that represents series of substantially parallel adjacent cross-section planes from throughout the volume of the hand with position data to locate the cross-section planes in space. Combination of these slices creates 3D data structures and images for volumetric data analysis. After "pre-processing" (a process that may comprise noise reduction and converting reflected ultrasound data from Polar coordinate system to Cartesian coordinate system, and possibly other data processing steps depending on the capabilities of the equipment used), the acquired scan represents the coordinates of 3D points that are derived from the surfaces of the hand bones. The coordinates of points are defined in relation to the absolute coordinate system (see FIG. 3, #14) that is predefined by the scanner.

The suggested method, for descriptive purposes only, considers that the cross-section planes are orthogonal to Y-axis that is directed (see FIG. 3) from the hand base to the tips of the fingers. The distance between planes is equal to a pre-set resolution tolerance. The sequence processing of data starts from the tips of the fingers but is not limited to other directions. Each cross-section (FIG. 3, #12) contains points (FIG. 3, #13) from the surfaces of all the bones that it runs through.

FIG. 1, Step 3: "Building the Normalized Template of the Hand Bone Set":

This step may be carried out using the method illustrated in FIG. 2 that is described below in detail.

Figure 2:
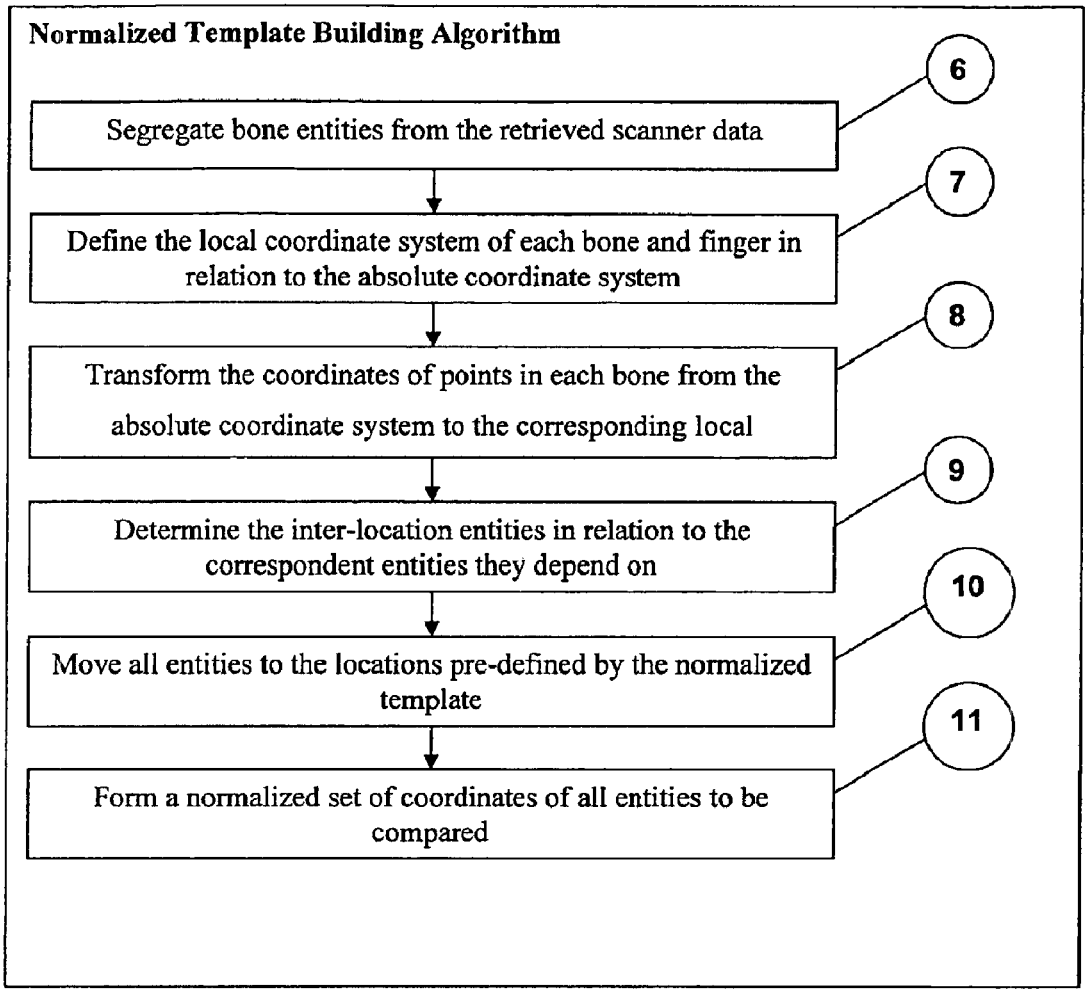
FIG. 2 is a schematic illustration of a method used for the building of a normalized template in accordance with the method of FIG. 1.

FIG. 2, Step 6: "Segregate Bone Entities from the Acquired Scanner Data".

Figure 4:
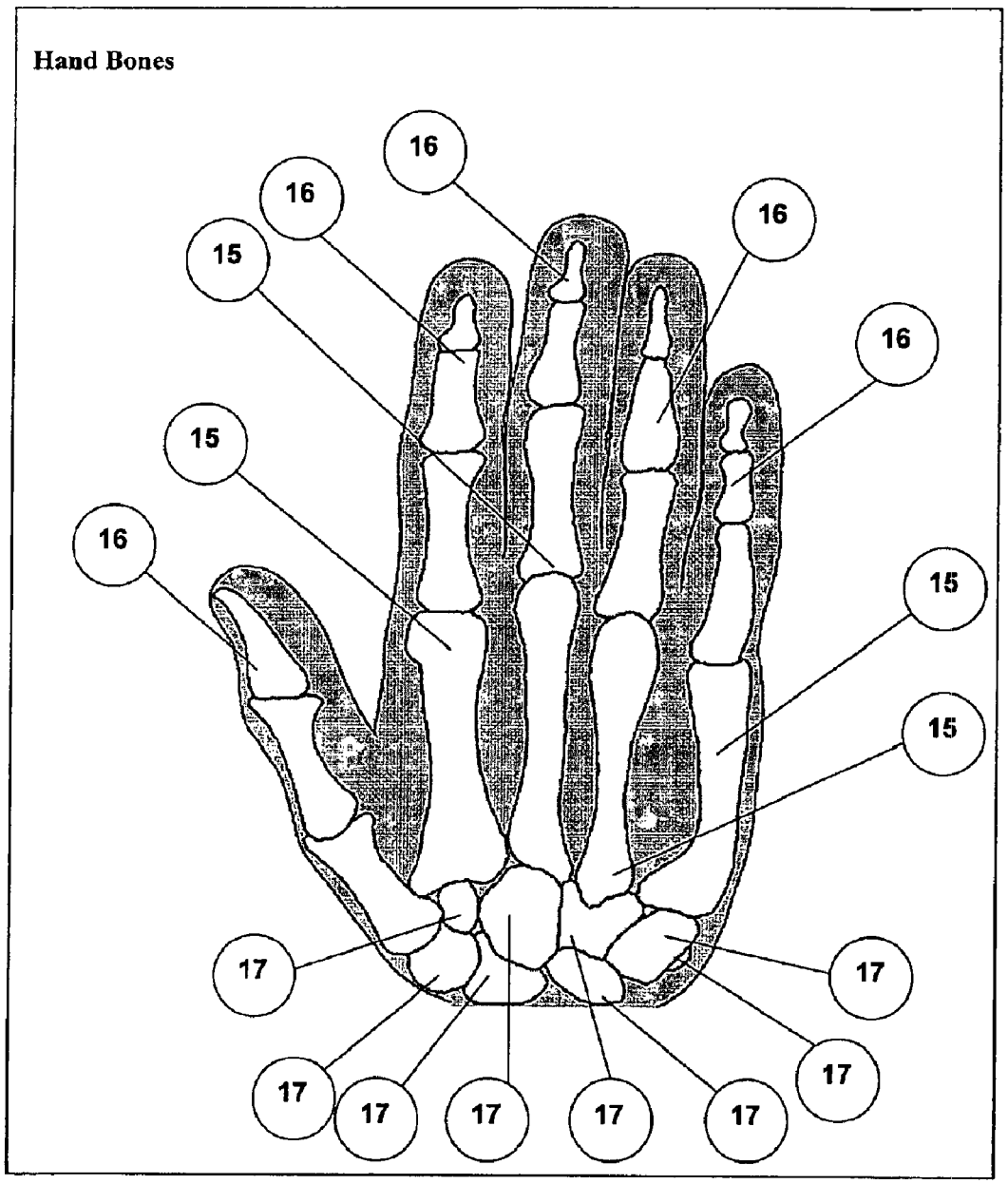
FIG. 4 is a top plan view of the hand of FIG. 3 identifying the bones of the hand.

The Entity Segregation Algorithm assesses the values of the coordinates of points in relation to the location proximity and attributes the points to the appropriate bone entities. The purpose of this step of is to restructure the retrieved data into a set of entities that identifies all 27 bones of the hand (8 carpal bones (FIG. 4, #17), 5 metacarpal bones (FIG. 4, #15), and 14 phalanges (FIG. 4, #16)). The 5 metacarpal bones and 14 phalanges are then joined to form the entities known as the fingers.

The Sequence of Processing is as Follows:

Firstly, points are arranged by values of coordinate Y. Points with the same coordinate Y are then arranged by values of combinations of coordinates X & Z to form closed sequences defining the current cross-section of the bone surface.

Secondly, points of one bone entity are separated from points of other bone entities along the X coordinate. The algorithm processes the values of coordinates within the predefined resolution tolerance and concludes the manner of grouping/segregating bone entities in relation to their location proximity. (i) If the location of two points is within the resolution tolerances, they are grouped in the same bone entity. (ii) If the distance along the X coordinate of the next point in line is greater than the resolution tolerance, it is grouped within the next bone entity. (iii) If the distance along the X coordinate is less than the tolerance, it is further analyzed by Z coordinates to assess the mode of direction. If the current direction is contrary to the previous direction with a steep gradient, then the point is grouped within the next bone entity, otherwise it is grouped in the same bone entity.

Figure 5:
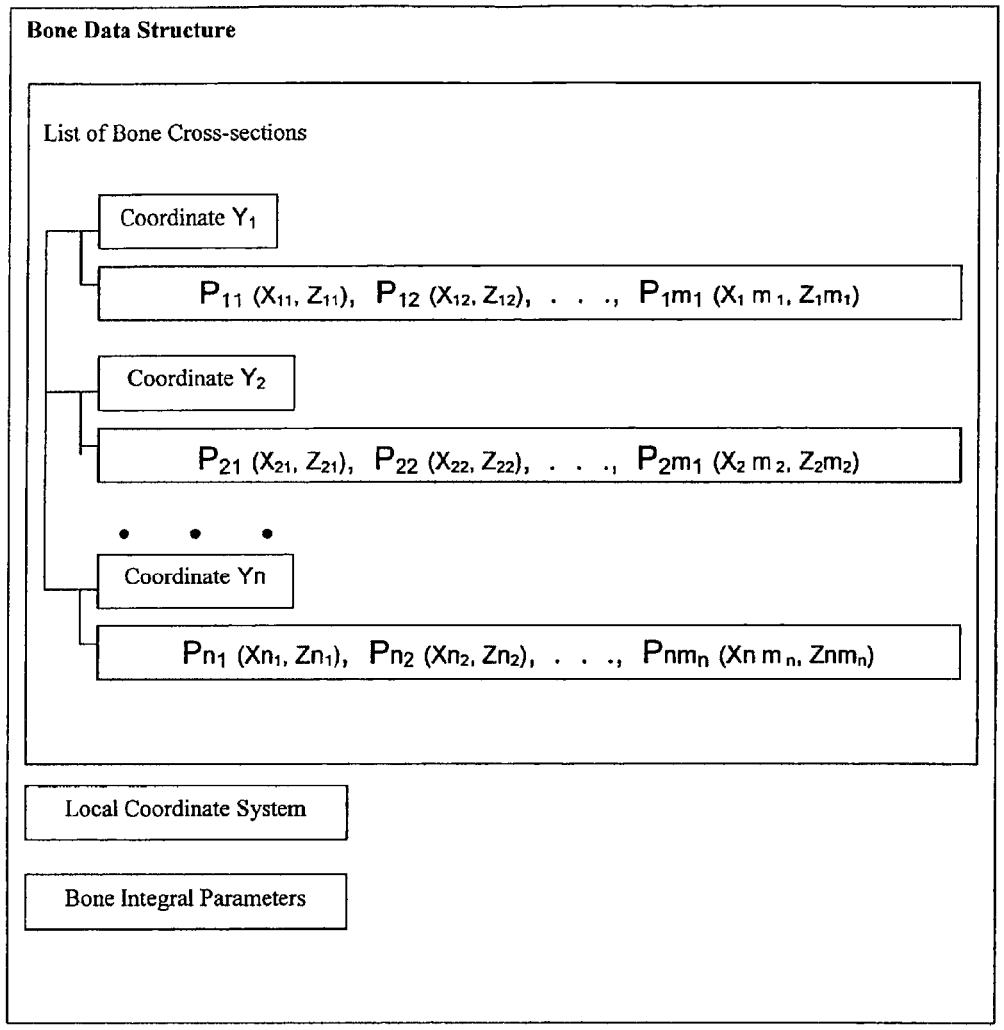
FIG. 5 is an illustration of a data structure of the points of FIG. 3.

Thirdly, the categorization of a bone entity within a finger element, (i.e. separating the Distal, Middle, Proximal, and Metacarpal bones from each other) is conducted. The algorithm analyzes the characteristics of points in terms of size, or area of cross-section of a particular sequence of points. A finger bone entity is defined by a set of cross-sections as illustrated in FIG. 5. The algorithm begins with the largest value of Y coordinates and ends with the smallest value of Y coordinates, and determines the diameter of each cross-section of the bone entity. The cross-section with the largest Y coordinate will define the start of the bone entity. Each diameter is then evaluated along the Y coordinate, and is added to the same entity, until the diameter value of the cross-section reaches the pre-defined 0 value. This Y coordinate will define the end of the current entity and the start of a new entity if it exists. This procedure is repeated to separate all the entities in a finger. Segregation of the carpal bones is performed in a similar manner.

Bone data structure entails: Bone Cross-sections, Bone Integral Parameters, and the Local coordinate system, is illustrated in FIG. 5. Each element of the list of bone cross-sections consists of two members: a number that represent a value of Y coordinate of the cross-section that is common to its points, and a list of X, Z coordinates of all points of the cross-section. The number of points varies for different cross-sections, depending on their size. The set of integral parameters of a bone may contain but is not limited to measurements and calculated values to define the characteristics of a bone as a unit. The local coordinate systems of bone entities determine positions of the entities in relation to other bones that they depend on with an exception of carpal and metacarpal bones that depend only on the absolute coordinate system.

Figure 6:
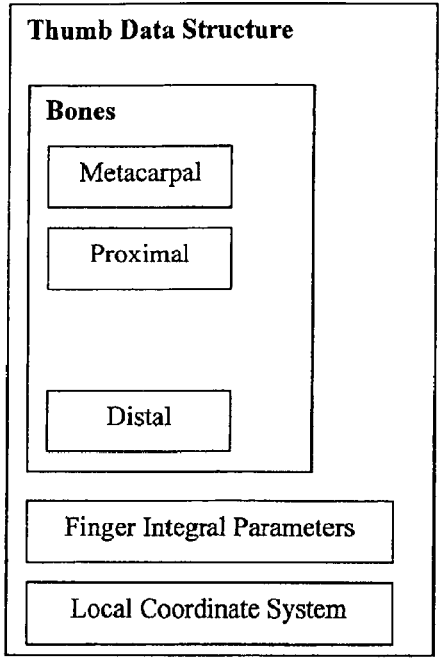
FIG. 6 is an illustration of a thumb data structure.
Figure 7:
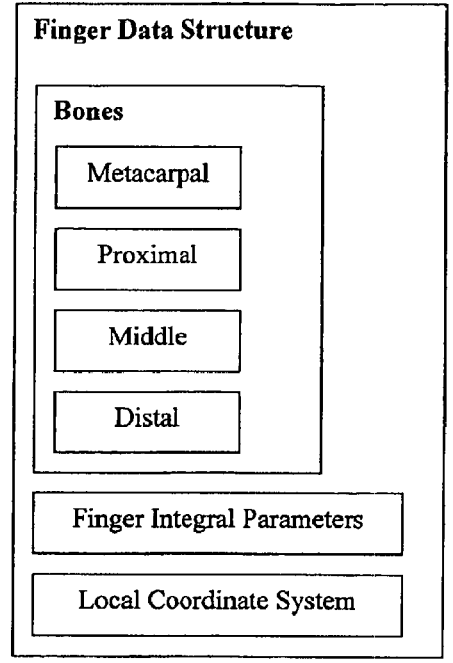
FIG. 7 is an illustration of a finger data structure.

Thumb and Finger data structures as illustrated in FIG. 6 and FIG. 7 entails: Bones, Integral Parameters and the local coordinate system. The integral parameters and the local coordinate systems are represented in the same manner as those in the Bone Data Structure. The variance in structure is that the thumb has no middle phalange, whereas the finger consists of Distal, Middle, and Proximal phalanges, and Metacarpal bones. The local coordinate systems for the thumb and finger are coincident with those of the corresponding Metacarpal bones.

Figure 8:
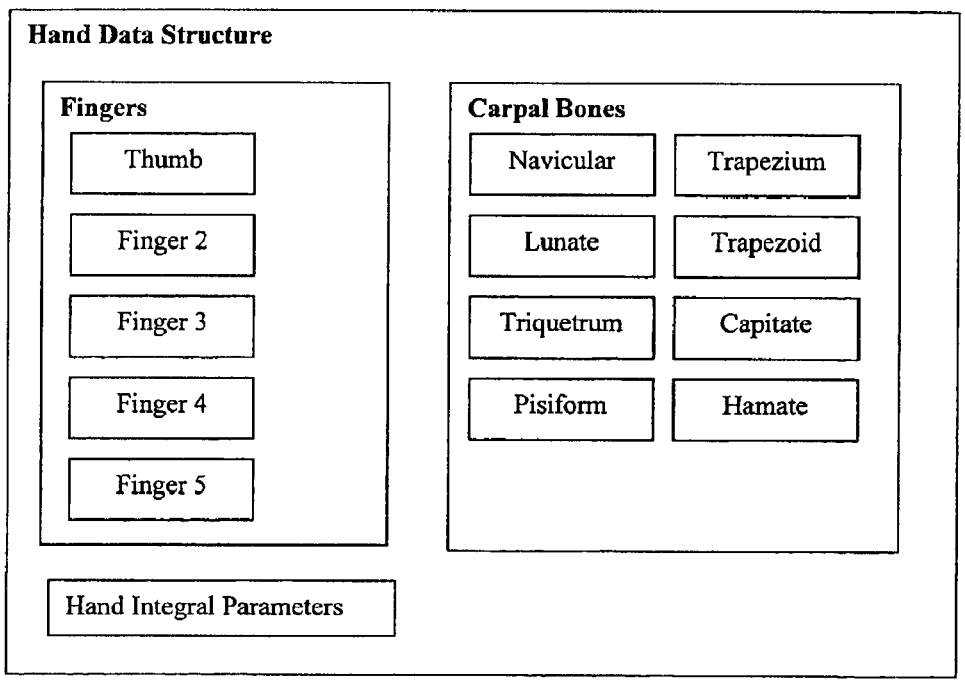
FIG. 8 is an illustration of a hand data structure.

Hand Data Structure, and its components are illustrated in FIG. 8. Its integral parameters define the characteristics of the hand as an entity.

FIG. 2, Step 7: "Define the Local Coordinate System of Each Bone and Finger in Relation to the Absolute Coordinate System"

The algorithm seeks the two points at the surfaces of the bone entity with the largest distance between them, and sets an imaginary axis (FIG. 9, #18) between these two points. If there is more than one set of points that fits the profile of the imaginary axis #18, then the line joining the centers of two polygons formed by the ends of such lines would become the imaginary axis.

The algorithm then seeks the largest diameter of the bone (FIG. 9, #19) that is orthogonal to axis #18. It should be noted that if more than one diameter fitting the profile exists, then the method above applies.

Figure 9:
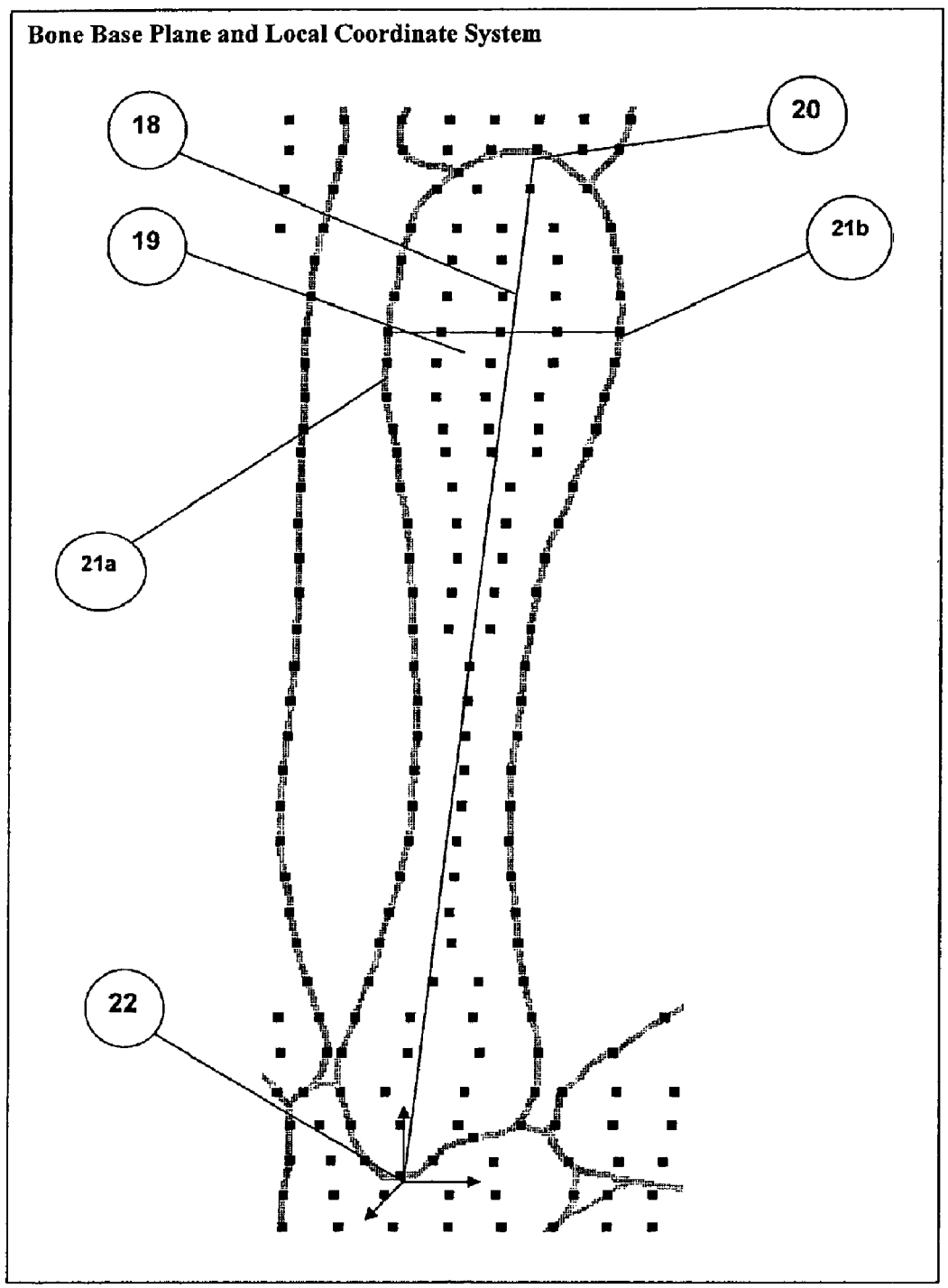
FIG. 9 is a top plan view of a bone and acquired points derived from the surface of the bone, showing a base plane of the bone and a local coordinate system of the bone.

Points #20, #21a and #21b of FIG. 9 will define the bone base plane. Point #21a and #21b represent the diameter #19. Point #20 represents the end of axis #18 that is closer to the tip of the hand. As the bone base plane is constant in relation to its bone entity, then it becomes the defining factors of positioning of the bone itself. Point #22 the other end of axis #18 becomes the origin of the bone local coordinate system with its end preset with rotational angles in relation to the base plane.

Figure 10:
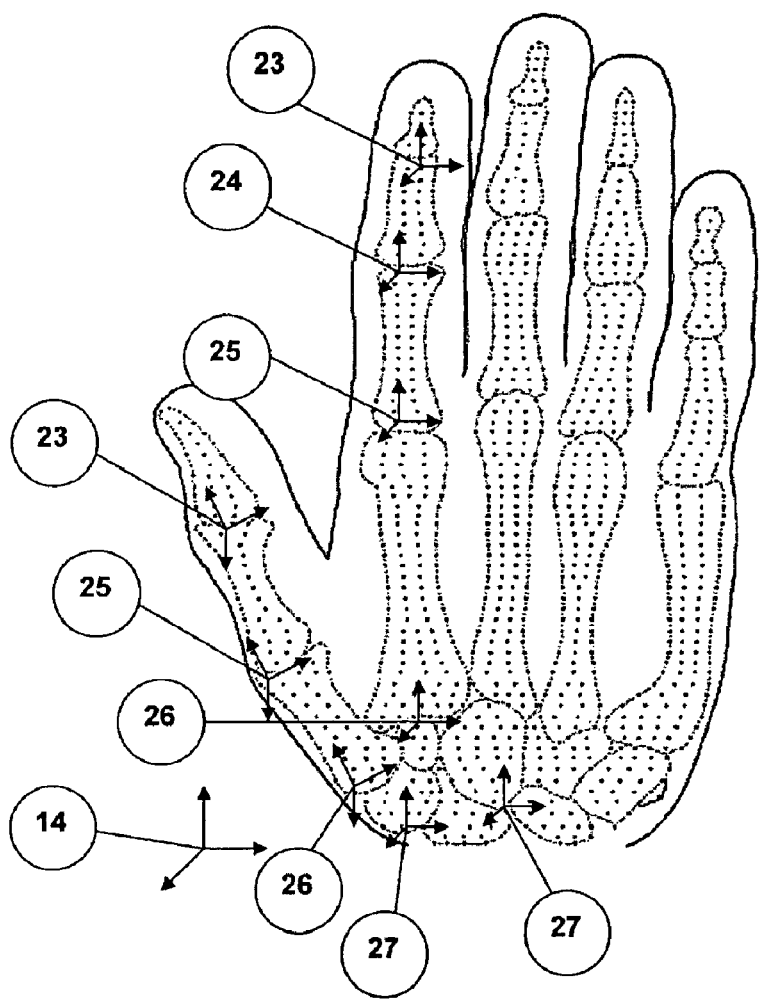
FIG. 10 is a top plan view of the hand of FIG. 3 showing local coordinate systems in relation to the absolute coordinate system of the hand.

FIG. 10 illustrates the local coordinate systems of the bone entities. The local coordinate systems of distal phalanges #23 determine positions of the entities in relation to the local coordinate system of the corresponding proximal phalange #25 of the thumb or of the middle phalange #24 of other fingers. Further, the local coordinate systems of the middle phalanges #24 determine positions of the entities in relation to the local coordinate system of the corresponding proximal phalanges #25 of the finger. The local coordinate systems of the proximal phalanges #25 determine positions of the entities in relation to the local coordinate system of the corresponding metacarpal bone #26 of the finger. And at last, the local coordinate system of each metacarpal bone and of the corresponding finger entities #26, and the local coordinate system of each carpal bone #27 determine positions of the entities in relation to the absolute coordinate system. The position of all coordinate systems are not limited to those that have been shown in FIG. 3, FIG. 9, and FIG. 10.

FIG. 2, Step 8: "Transform the Coordinates of Points in Each Bone from the Absolute Coordinate System to the Corresponding Local Coordinate System"

The position of each local coordinate system relating to the absolute coordinate system is determined by its transformation matrix. To obtain the coordinates of points in relation to the local coordinate system, the vector defining these points in the absolute coordinate system is multiplied by the inverted transformation matrix.

FIG. 2, Step 9: "Determine the Inter-Location Entities in Relation to the Corresponding Entities they Depend on"

The location is calculated for entities that belong to the same finger and depend on each other. These inter-locations are compared with the inter-location that has been chosen for a normalized template and the corresponding transformation matrices are formed.

FIG. 2, Step 10: "Move all Entities to the Locations Pre-Defined by the Normalized Template"

Figure 11:
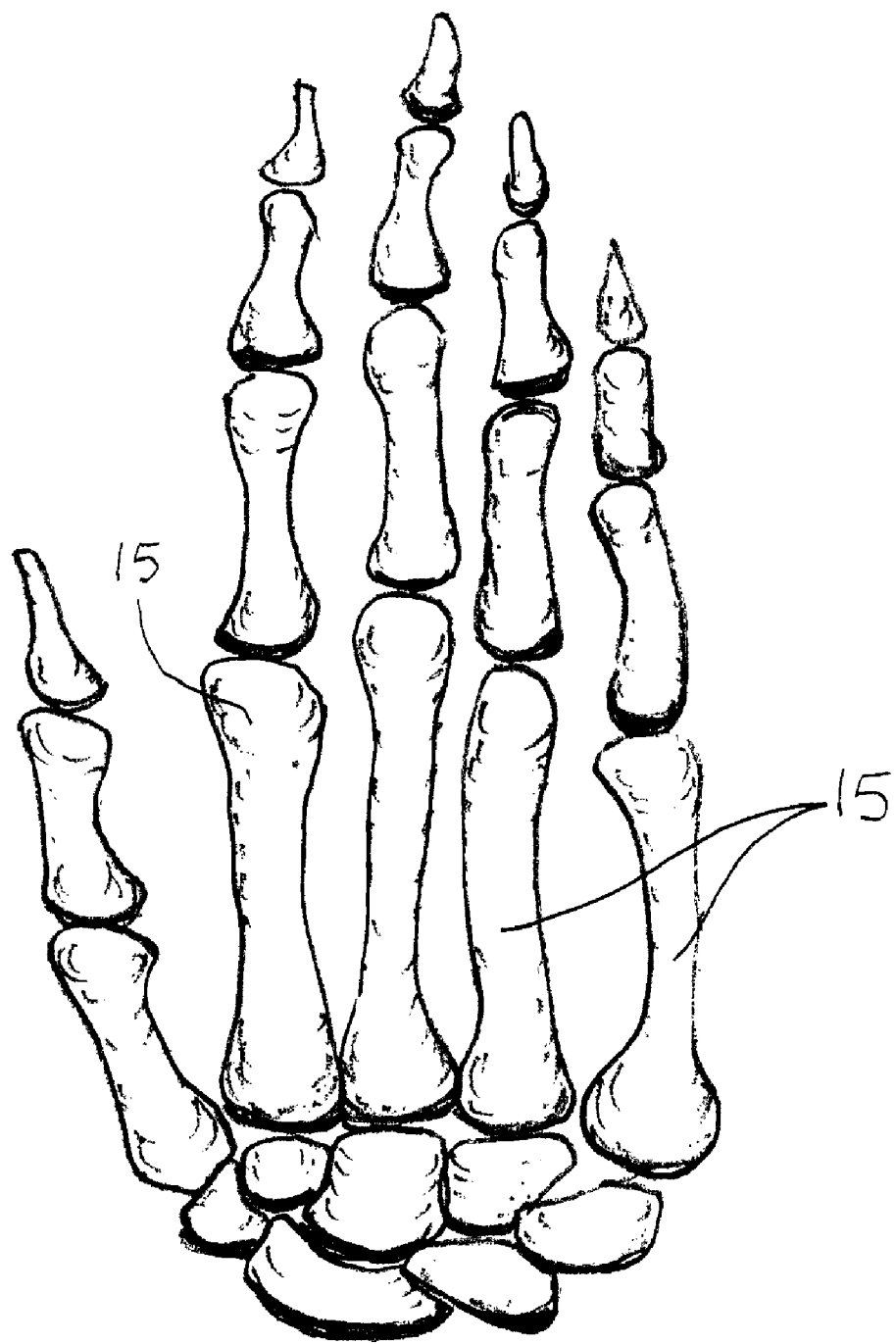
FIG. 11 is a top plan view of a rendered three dimensional model of hand bone geometry in accordance with the normalized template.
Figure 12:
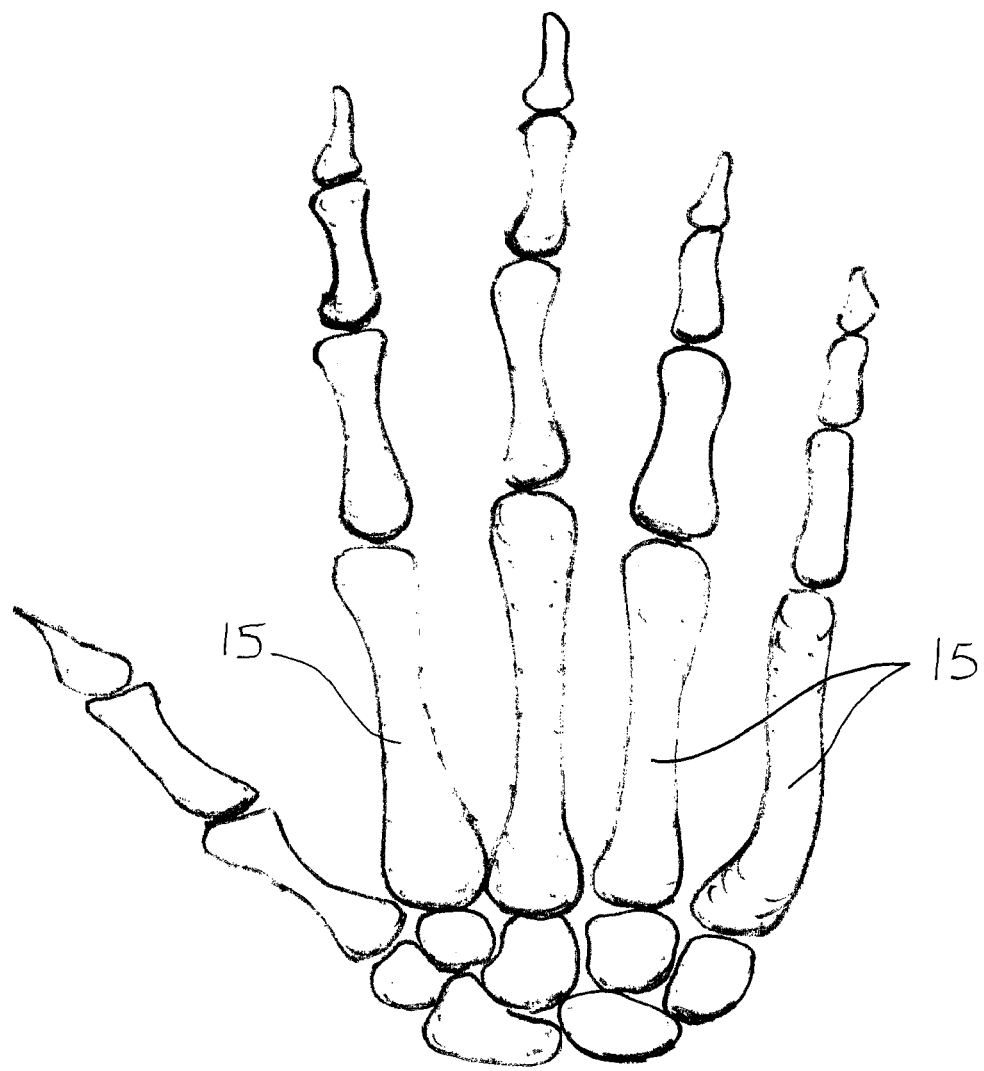
FIG. 12 is a top plan view of the rendered three dimensional model of FIG. 11 prior to the transformation based on the normalized template.
Figure 13:
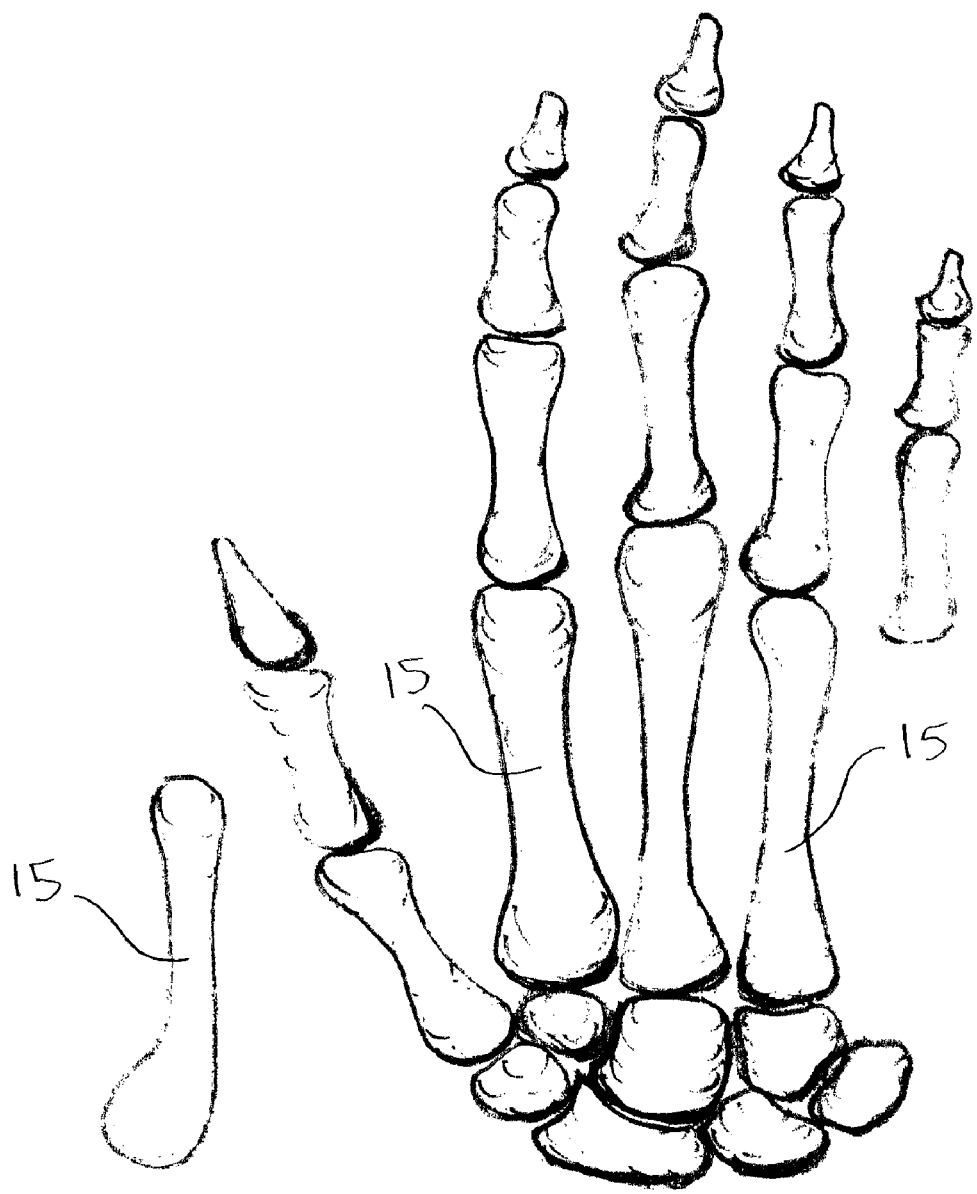
FIG. 13 is a top plan view of the rendered three dimensional model of FIG. 11 during an intermediate step of the transformation in accordance with the normalized template.

Via the stepwise process of multiplying the vectors defining the location of bone entities to the corresponding transformation matrices, the algorithm moves all bone entities to the locations predefined by a definition of the normalized template as illustrated in FIGS. 11-13.

This way the method accounts for possible rotations of distal phalange in relation to the corresponding proximal bone of the thumb or the corresponding middle phalange of other fingers comparing with the pre-defined normalized template inter-locations. The algorithm then accounts for possible rotations of all distal and middle phalanges of all fingers except the thumb in relation to the corresponding proximal phalanges, comparing with the pre-defined normalized template inter-locations. After that, the algorithm accounts for possible rotations of all distal, middle, and proximal phalanges of all fingers (or distal and proximal phalanges for the thumb) in relation to the corresponding metacarpal bones comparing with the pre-defined normalized template inter-locations of these entities. This way the method accounts for possible combined rotations of fingers in relation to the corresponding metacarpal bones.

Further, for the set of carpal and metacarpal bones, their positions relating to the absolute coordinate system are compared with the positions that have been chosen in a normalized template. If the positions are different, the corresponding transformation matrix is formed and all these bones and all finger bones that depend on them are moved to the location pre-defined by the definition of the normalized template. This way, the method accounts for possible rotations and translation of whole hand in relation to the pre-defined location at the scanner platen.

As a result, all coordinates of all points of the bones have been accordingly changed to meet the conditions of the normalized template.

FIG. 2, Step 11: "Form a Normalized Set of Coordinates of all Entities to be Compared"

At this stage, all the bone entities are defined by the cross-sections that were perpendicular to the Y-axis as it was defined in the data set acquired from the scanner. However since acquisition, all bone entities may drift location. The algorithm is designed to redefine all points at the surfaces of bone entities accounting for such a drift to place them at the same pre-defined cross-section planes.

These new points are placed at the same locations for every scanning attempt allowing for the comparison of the content of data received from different sources.

Now the algorithm has finished building of the normalized template (see FIG. 1, step 3).

According to the steps described above, a model of bone geometry of a volumetric region of the body such as a hand can be produced (FIG. 1, Steps 1-3). First, the volumetric region is scanned using ultrasound and geometric data associated with bones within the volumetric region is acquired (FIG. 1, Step 2). Depending on the scanning technique used, the points of the acquired data may lie within a plurality of planes or slices extending through the volumetric region. Points derived from at least one surface of the bones is identified from the acquired data. Optionally, the acquired data may be pre-processed to reduce noise (FIG. 1, Step 2). The points are then organized into separate bone entities representing the bones of the volumetric region (FIG. 1, Step 3). Then, the points are transformed so as to position the bone entities in accordance with a normalized template (FIG. 1, Step 3). The points may then be stored on a record carrier for future use.

The transformation of the points may be conducted by firstly defining a local coordinate system for each bone entity in relation to an absolute coordinate system of the volumetric region (FIG. 2, Step 7); transforming the points for each bone entity from the absolute coordinate system to their respective local coordinate systems (FIG. 2, Step 8); determining relative locations of the bone entities based on a normalized template (FIG. 2, Step 9); and transforming the acquired data so as to move the bone entities to their relative locations (FIG. 2, Step 10).

FIG. 11 illustrates a three dimensional projection of a model of a hand bone transformed according to the normalized template as it is produced by an Surface Rendering Algorithm. This algorithm is optionally used when the new hand bone template is recorded. To produce this image, the Surface Rendering Algorithm was created that forms a surface of the entities approximating it by triangular polygons. The algorithm creates the surface by rendering a sets of polygons to the screen accordingly to the sequence of the points of each couple of adjacent cross-sections.

During scanning and acquisition of hand bone geometry data, the volumetric region to be scanned may not be positioned exactly at the same position each time it is scanned. Accordingly, the acquired data may have to be transformed in accordance to the normalized template in order to be used to conduct a meaningful comparison with previously acquired geometric models or templates that are stored on a record carrier. For example, FIG. 11 shows a rendered three dimensional model of hand bone geometry in accordance with a normalized template and FIG. 12 shows a model of acquired hand bone geometry prior to the transformation based on the normalized template. FIG. 13 shows the model of acquired hand bone geometry during an intermediate step of the transformation (FIG. 2, Steps 7-10) in accordance with the normalized template.

FIG. 1, Step 4: "Determining the Integral Parameters"

The algorithm may also calculate integral parameters of the bone geometry. These parameters may include, but are not limited to simple measurements such as length/width of a bone or a group of bones, or some results of calculations such as ratio of length to width or other more complex mathematical processing.

The algorithm proceeds with a calculation of the fingers integral parameters using the previously calculated bone integral parameters. Next, it calculates the hand integral parameters using the previously calculated bone and finger integral parameters. The integral parameters may be used for comparison purpose as described below.

FIG. 1, Step 5: "Comparing the Normalized Template with those Previously Stored and Determining Whether the Subject was Verified/Identified"

The geometric model produced above and/or integral parameters derived from the geometric model may be used for comparison with previously acquired and stored geometric models (templates) for the purpose of identifying a person or verifying the identity of a person.

For example, the identification of a person based on ultrasound scan analysis of bone geometry may be conducted by firstly scanning a volumetric region such as a hand of the person using ultrasound and acquiring geometric data associated with bones within the volumetric region. Points derived from a surface of the bones may be identified from the acquired data. The points may be organized into separate bone entities representing the bones of the volumetric region and then transformed so as to position the bone entities in accordance with the normalized template. Then, a search may be conducted through previously stored geometric data comprising a plurality of templates, to determine if a match exists between the points of the acquired data and one of the templates. The points of the acquired data may be three-dimensional and lie within a plurality of planes extending through the volumetric region.

The algorithm searches in the record carrier for a template that is substantially identical to the obtained normalized template. This process can be accomplished in different ways. The determination of whether a match exists may advantageously be done by comparing an integral parameter of the acquired data with an integral parameter of the previously stored geometric data. Accordingly, in the case of the identification task, the search may be accelerated using the key string built on the base of the integral parameters.

In case of verification, a person shall present by any means his/her identity information. The system will retrieve the corresponding template of the person from the record carrier in preparation for the comparison attempt with the identity record. If no such identity record exists, or the identity of the person attempting the verification is falsified, then the verification will be rejected.

Hence, the verification of a person's identity based on ultrasound scan analysis of bone geometry may be conducted by firstly scanning a volumetric region such as a hand of the person using ultrasound and acquiring geometric data associated with bones within the volumetric region. Points derived from a surface of the bones may be identified from the acquired data. The points may be organized into separate bone entities representing the bones of the volumetric region and then transformed so as to position the bone entities in accordance with the normalized template. The points of the acquired data may then be compared to previously stored geometric data in order to determine if a match exists. The previously stored geometric data may comprise a previously stored template that is retrieved by entering a personal identifier of the person. The identifier may comprises an identification number, name, address or other suitable means of associating a particular template to a person.

Again, the points of the acquired data may be three-dimensional and lie within a plurality of planes extending through the volumetric region. The comparison may be done by determining integral parameters of at least one of the bones from the acquired data and comparing it with a corresponding integral parameter of the template retrieved from the record carrier.

The above description is meant to be exemplary only, and one skilled in the art will recognize that changes may be made to the embodiments described without departing from the scope of the invention disclosed. For example, even though the above example refers to the acquisition and the comparison of three-dimensional data, it is understood that the geometric model of bone geometry could also comprises two-dimensional data such as a two-dimensional outline of bone geometry. One skilled in the art will recognize that a meaningful comparison could be done using acquired two-dimensional geometric data and comparing it with previously stored two-dimensional geometric data. Still other modifications which fall within the scope of the present invention will be apparent to those skilled in the art, in light of a review of this disclosure, and such modifications are intended to fall within the appended claims.

What is claimed is:

1. A method for producing a model of bone geometry of a volumetric region of a body, the method comprising the steps of:
   a) scanning the volumetric region using ultrasound and acquiring geometric data associated with bones within the volumetric region;
   b) identifying points from the acquired data that are derived from a surface of the bones;
   c) organizing the points into separate bone entities representing the bones of the volumetric region; and
   d) transforming the points so as to position the bone entities in accordance with a normalized template.

2. The method as defined in claim 1, wherein the identifying step b) comprises the step of pre-processing the acquired data to reduce noise.

3. The method as defined in claim 1, wherein the points are three-dimensional.

4. The method as defined in claim 1, wherein step d) comprises:
   i) defining a local coordinate system for each bone entity in relation to an absolute coordinate system of the volumetric region;
   ii) transforming the points for each bone entity from the absolute coordinate system to their respective local coordinate systems;
   iii) determining relative locations of the bone entities based on a normalized template; and
   iv) transforming the acquired data so as to move the bone entities to their relative locations.

5. The method as defined in claim 1, wherein the volumetric region and the normalized template define the geometry of at least a portion of a hand.

6. The method as defined in claim 1, further comprising the step of storing the points.

7. The method as defined in claim 1, wherein the points of the acquired data lie within a plurality of planes extending through the volumetric region.

8. The method as defined in claim 1, further comprising the step of producing a rendered image of the bone geometry.

9. A method for verifying the identity of a person based on ultrasound scan analysis of bone geometry, the method comprising the steps of:
   a) scanning a volumetric region of the person using ultrasound and acquiring geometric data associated with bones within the volumetric region;
   b) identifying acquired points from the acquired data that are derived from a surface of the bones;
   c) organizing the acquired points into separate bone entities representing the bones of the volumetric region;
   d) transforming the acquired points into normalized points so as to position the bone entities in accordance with a normalized template; and
   e) comparing the normalized points to previously stored geometric data to determine if a match exists.

10. The method as defined in claim 9, wherein the previously stored geometric data is retrieved by entering a personal identifier of the person.

11. The method as defined in claim 10, wherein step e) comprises determining an integral parameter of at least one of the bones and comparing the integral parameter of the at least one of the bones with an integral parameter of the previously stored geometric data.

12. The method as defined in claim 9, wherein the points are three-dimensional.

13. The method as defined in claim 9, wherein the points of the acquired data lie within a plurality of planes extending through the volumetric region.

14. The method as defined in claim 9 further comprising the step of redefining the acquired data to account for drift.

15. The method as defined in claim 9, further comprising the step of determining an integral parameter of at least one of the bones to be used in the comparing step e).

16. The method as defined in claim 9, wherein step d) comprises:
   i) defining a local coordinate system for each bone entity in relation to an absolute coordinate system of the volumetric region;
   ii) transforming the points for each bone entity from the absolute coordinate system to their respective local coordinate systems;
   iii) determining relative locations of the bone entities based on a normalized template; and
   iv) transforming the acquired data so as to move the bone entities to their relative locations.

17. A method for identifying a person based on ultrasound scan analysis of bone geometry, the method comprising the steps of:
   a) scanning a volumetric region of the person using ultrasound and acquiring geometric data associated with bones within the volumetric region;
   b) identifying acquired points from the acquired data that are derived from a surface of the bones;
   c) organizing the acquired points into separate bone entities representing the bones of the volumetric region;

d) transforming the acquired points into normalized points so as to position the bone entities in accordance with a normalized template; and e) searching through previously stored geometric data comprising a plurality of templates, and, determining if a match exists between the points normalized and one of the templates.

18. The method as defined in claim 17, wherein the points are three-dimensional.

19. The method as defined in claim 18, wherein the points of the acquired data lie within a plurality of planes extending through the volumetric region.

20. The method as defined in claim 17, wherein step e) comprises comparing an integral parameter of the acquired data with an integral parameter of the previously stored geometric data.

* * * * *